United States Patent [19]

Göschke

[11] Patent Number: 4,654,340
[45] Date of Patent: Mar. 31, 1987

[54] PYRIDAZINONES, PHARMACEUTICAL PREPARATIONS CONTAINING THESE COMPOUNDS, AND THE USE THEREOF

[75] Inventor: Richard Göschke, Bottmingen, Switzerland

[73] Assignee: Ciba-Geigy Corporation, Ardsley, N.Y.

[21] Appl. No.: 859,684

[22] Filed: May 5, 1986

Related U.S. Application Data

[63] Continuation of Ser. No. 758,833, Jul. 24, 1985, Pat. No. 4,613,599, which is a continuation of Ser. No. 608,536, May 9, 1984, abandoned, which is a continuation of Ser. No. 490,993, May 2, 1983, abandoned, which is a continuation-in-part of Ser. No. 352,739, Feb. 26, 1982, abandoned.

[30] Foreign Application Priority Data

Mar. 4, 1981 [CH] Switzerland .................. 1443/81

[51] Int. Cl.$^4$ .................. A61K 31/535; C07D 413/10
[52] U.S. Cl. .................................... 514/234; 544/114
[58] Field of Search ..................... 544/114; 514/234

[56] References Cited

U.S. PATENT DOCUMENTS 3,975,388  8/1976  Hakim et al. .................. 544/114

FOREIGN PATENT DOCUMENTS 1488330 10/1977 United Kingdom .

OTHER PUBLICATIONS

Curran et al., Chemical Abstracts, vol. 77 (1972), No. 19664f.

Primary Examiner—Robert W. Ramsuer
Attorney, Agent, or Firm—Michael W. Glynn; Irving M. Fishman

[57] ABSTRACT

The invention concerns compounds of formula I

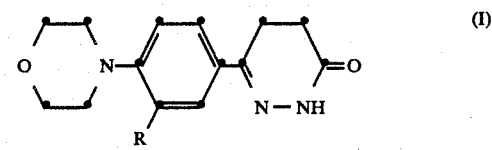

wherein R is a fluorine, bromine or iodine atom or the amino, acetylamino, methyl, cyano, hydroxyl, methoxy or trifluoromethyl group, the tautomeric forms thereof, and acid addition salts of the compounds in which R represents amino. The products have antithrombotic activity. They can be prepared according to methods known per se.

5 Claims, No Drawings

PYRIDAZINONES, PHARMACEUTICAL PREPARATIONS CONTAINING THESE COMPOUNDS, AND THE USE THEREOF

This is a continuation of application Ser. No. 758,833 filed on July 24, 1985, now U.S. Pat. No. 4,613,599, which in turn is a continuation of application Ser. No. 608,536 filed May 9, 1984 now abandoned, which is turn is a continuation of application Ser. No. 490,933 filed May 2, 1983 now abandoned, which in turn is a continuation-in-part of application Ser. No. 352,739 filed Feb. 26, 1982 now abandoned.

The present invention relates to novel pyridazinones, especially to 4,5-dihydro-3(2H)-pyridazinones, to the production thereof, to pharmaceutical preparations which contain these novel compounds, and to their use.

German Offenlegungsschrift No. 2,207,517 has a subject matter, inter alia, 6-phenyl-4,5-dihydro-3(2H)-pyridazinones which are substituted in the p-position in the phenyl group by a heterocycle, and which exhibit antihypertensive activity.

It has now been found that the novel compounds of the general formula I

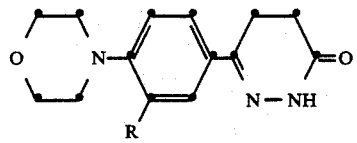

wherein R is a fluorine, bromine or iodine atom, or the amino, acetylamino, methyl, cyano, hydroxyl, methoxy or trifluoromethyl group, and the tautomeric forms thereof, surprisingly have a marked antithrombotic action.

The compounds of the formula I have valuable pharmacological properties. They thus exhibit for example a pronounced antithrombotic action. This can be demonstrated for example on the guinea pig by virtue of the suppression of thrombocytopenia after induction by means of ADP (Thromboembolism, Edited by J. R. Mitchell and J. G. Doment, Academic Press (1977), p. 36) in the dose range of about 30 to 300 mg/kg p.o., on the basis of the Forssman reaction (Thrombosis, Haemostasis 42, 100 (1979)) in the dose range of about 100 to 300 mg/kg p.o., and on the basis of the suppression of the thrombosis forming on a cotton thread in an extracorporeal shunt on the rat (method analogous to Brit. J. Pharmacol., 73, 219 P (1981)) in the dose range of about 5 to 50 mg/kg p.o., as well as by virtue of the suppression of the platelet aggregation, induced ex vivo by collagen or arachidonic acid, after prior peroral administration of the active substance in doses of 50 to 300 mg/kg. The compounds of the general formula I are accordingly suitable in particular for the treatment of thrombotic diseases, and can be used as active ingredients in antithrobotic pharmaceutical preparations.

Of particular interest in this invention are compounds in which R is cyano or the acetamino group. To be mentioned especially is 6-(3-cyano-4-morpholino-phenyl)-4,5-dihydro-3(2H)-pyridazinone or 6-(3-acetamino-4-morpholino-phenyl)-4,5-dihydro-3(2H)-pyridazinone. Also of special interest are compounds of the formula I in which R is an amino, or a bromine atom such as 6-(3-amino-4-morpholino-phenyl)-4,5-dihydro-3(2H)-pyridazinone, 6(4-morpholino-3-bromophenyl)-4,5-dihydro-3(2H)-pyridazinone.

The novel pyridazinones of the formula I are produced by methods known per se.

The novel compounds of the formula I can thus be obtained by reacting a ketocarboxylic acid of the formula II

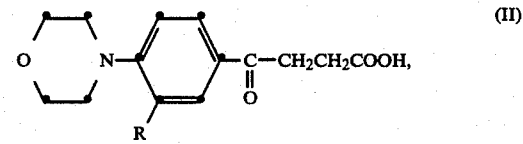

or a reactive derivative of such a ketocarboxylic acid, with hydrazine. There is preferably used hydrazine hydrate in hydrate form, which when used in excess can also simultaneously serve as solvent. It is however more advantageous to add an additional solvent. Suitable inert solvents are preferably alcohols, for example: methanol, ethanol, isopropanol, n-butanol, isoamyl alcohol, glycols and ethers thereof, such as ethylene glycol, diethylene glycol, ethylene glycol monomethyl ether or -monoethyl ether (methyl glycol or ethyl glycol), also ethers, especially water-soluble ethers, such as tetrahydrofuran, dioxane or ethylene glycol dimethyl ether (diglymes); and also water, as well as mixtures of these solvents with one another, particularly mixtures with water, for example aqueous ethanol. The reaction temperatures are advantageously between about 20° and about 200° C., preferably between 60° and 80° C.

Suitable reactive derivatives of the ketocarboxylic acid of the formula II are for example the esters, in particular lower alkyl esters, such as methyl or ethyl ester. It is also possible to use the acid amides and acid halides of acids of the formula II, especially the acid chlorides or acid bromides. Further suitable reactive derivatives of the carboxylic acid of the formula II can be formed in situ during the reaction. These include for example the hydrazones of the formula $R_1$—C(=N—NH$_2$)—CH$_2$—CH$_2$—COOH, the hydrazides of the formula $R_1$—CO—CH$_2$—CH$_2$—CO—NH—NH$_2$ and the hydrazones of the hydrazides of the formula

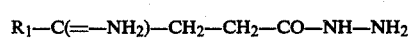

$R_1$—C(=NH$_2$)—CH$_2$—CH$_2$—CO—NH—NH$_2$ wherein $R_1$ is the radical

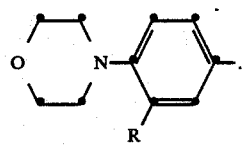

The starting materials formed in situ are produced from the ketocarboxylic acids of the formula II, and are not isolated from the reaction mixture but further reacted to the compounds of the formula I.

The compounds of the formula I can also be obtained by reacting compounds of the formula III

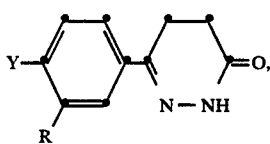

(III)

wherein R has the meaning defined under the formula I, and Y is a group detachable together with hydrogen, with morpholine. The employed morpholine is advantageously used as a free base in excess; it can however also be used in the form of an acid addition salt, for example as a hydrohalide, such as hydrochloride.

With use of only a slight excess of morpholine as a free base, or with use of the morpholine as an acid addition salt, it is advantageous to additionally add a stoichiometrically equivalent amount of for example a tertiary alkylamine, such as triethylamine or N-ethyldiisopropylamine.

The described reaction of compounds of the formula III with morpholine is performed optionally in the presence of a solvent, preferably an aprotic solvent. Examples of solvents preferably used are ethers, for example diethyl ether and tetrahydrofuran, especially aliphatic ketones and esters, such as acetone, methyl ethyl ketone and ethyl acetate, aromatic hydrocarbons, for example benzene, toluene or xylene, as well as acetonitrile. The reaction is particularly preferably carried out in diethyl ether or in acetonitrile.

The reactions can be performed at a temperature of between 0° and 150° C., preferably however between room temperature and the reflux temperature of the reaction mixture.

A group Y detachable together with hydrogen is for example in particular a free or preferably etherified mercapto group, also an optionally reactive, functionally modified hydroxyl group or the nitroamino group. An etherified mercapto group is especially a mercapto group etherified by an unsubstituted or substituted hydrocabon, particularly one of aliphatic character. It is especially lower alkylthio, for example methylthio, ethylthio or butylthio, or phenyl-lower-alkylthio, for example phenylthio or benzylthio. An optionally reactive, functionally modified hydroxyl group is a free hydroxyl group or, for example, a corresponding esterified hydroxyl group. This is for example halogen, such as chlorine or bromine, or lower alkylsulfonyloxy, for example methanesulfonyloxy.

As a group detachable together with hydrogen, Y is preferably a halogen atom, for example chlorine or bromine.

Compounds of the general formula I can also be produced by reacting a compound of the formula VI

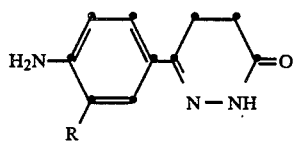

(IV)

with a diethyl ether derivative of the formula V

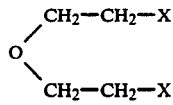

(V)

wherein X is a group detachable together with hydrogen.

The reaction of a compound of the formula IV with a compound of the formula V is performed preferably in the presence of an organic base, for example a tertiary alkylamine, such as triethylamine or N-ethyldiisopropylamine.

The described reaction of compounds of the formula IV with a compound of the formula V is performed optionally in the presence of a solvent, prefarbly a polar solvent, for example dimethylformamide.

The reactions can be carried out at a temperature of between 0° and 200° C., preferably however between room temperature and the reflux temperature of the reaction mixture.

A group X detachable together with hydrogen has already been defined above under the formula III for the symbol Y.

As a group detachable together with hydrogen, X is preferably a halogen atom, for example chlorine or bromine.

According to a further process, compounds of the formula I wherein R is a halogen atom with the exception of a chlorine atom or the cyano group can be produced by heating a compound of the formula VI

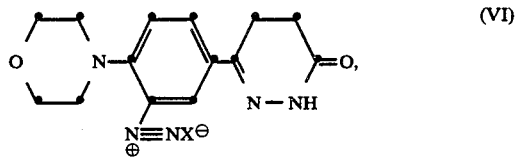

(VI)

werein $X^\ominus$ is an anion of a mineral acid, for example in the presence of copper or of a copper-I salt, for example a fluoride, bromide or iodide or cyanide. An anion of a mineral acid is for example the anion of a hydrohalic acid. In the case of the introduction of R as fluorine, $X^\ominus$ is a fluoride or tetrafluoroborate anion. The heating of a compound of the formula VI where X is a fluoride or tetrafluoroborate anion is performed in hydrofluoric acid or in tetrafluoroboric acid. With the introduction of a cyano group, the diazonium salt of the formula VI is for example reacted with copper-I cyanide, which is present as a complex with potassium cyanide in solution. For example, a diazonium salt of the formula VI is reacted with a mixture of potassium cyanide and copper-I sulfate. The liberating of the diazonium salt is effected thermally at temperatures of between 30° and 150° C., preferably between 30° and 40° C. when a diazonium fluoride is present, and between 100° and 150° C. when a diazonium tetrafluoroborate is present.

The diazotisation of aromatic amines is performed for example with an alkali metal nitrite, such as sodium nitrite, preferably with the aid of anhydrous sodium nitrite. Diazotisation is performed for example at a temperatures of between −10° and +10° C., preferably at a temperature of between 0° and +5° C. By reaction with a mineral acid, there are obtained compounds of the formula VI wherein X is an anion of a mineral acid.

According to a further process, compounds of the formula I wherein R is a fluorine, bromine or iodine atom can be produced by halogenating compounds of the formula VII

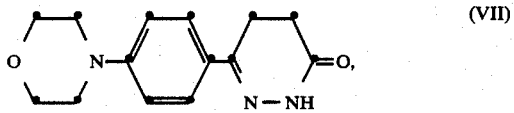

Halogenation can be performed on the one hand by the use of halogen, preferably in the presence of a Lewis acid, for example in the presence of an iron-III, aluminium, antimony-III or tin-IV halide; and on the other hand by means of a halogen carrier, for example in the presence of a heavy metal, such as iron, or with the use of a halogenating agent, for example in the presence of an oxidising agent, of an N-halo-imide, for example bromosuccinimide or -phthalimide.

The direct introduction of an iodine atom is performed, with the use of hydrogen iodide, in the presence of an oxidising agent, for example in the presence of nitric acid or mercury oxide.

The halogenation reactions mentioned are performed, depending on the halogen atom concerned, at temperatures of between −10° C. and the reflux temperature of the reaction mixture, preferably at a temperature of between −5° and +30° C.

Compounds of the formula I in which R is a free hydroxyl group or an amino group can also be obtained by solvolysing or hydrogenolysing a compound of the formula VIII

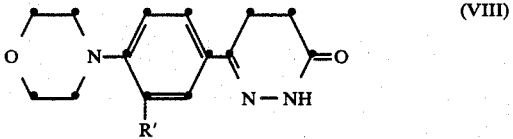

wherein R' is a readily solvolysable or hydrogenolysable ether group or acyloxy group, or amino group protected by a protective group.

An ether or acyloxy group which can be readily solvolysed or hydrogenolysed is for example an ether or acyloxy group which is detachable by solvolysis, including hydrolysis, acidolysis or alcoholysis, or by means of reduction, including hydrogenolysis.

An acyloxy group detachable by solvolysis is for example an acyloxy group in which the acyl moiety is the radical of an organic carboxylic acid, for example lower alkanoyl, such as acetyl, halo-lower-alkanoyl, such as haloacetyl, for example chloroacetyl, or carbamoyl, or aroyl, such as benzoyl, also the acyl moiety is the radical of a semi-ester of carbonic acid, such as lower-alkoxycarbonyl, for example methoxycarbonyl, ethoxycarbonyl or tert-butyloxycarbonyl, 2-halo-lower-alkoxycarbonyl, for example 2,2,2-trichloroethoxycarbonyl or 2-iodoethoxycarbonyl, unsubstituted or substitued 1-phenyl-lower-alkoxycarbonyl, for example benzyloxycarbonyl or diphenyl methoxycarbonyl or aroylmethoxycarbonyl, for example phenacyloxycarbonyl, also an unsubstituted or substituted 1-polyphenyl-lower-alkyl group, wherein substituents of the phenyl moiety can be for example lower alkyl or lower alkoxy, such as methyl or methoxy, and in particular trityl, or an organosilyl radical, especially trimethylsilyl.

An ether group which is detachable by solvolysis is for example lower alkoxy, for example methoxy or ethoxy or a 1-phenyl-lower-alkoxy group, such as benzyloxy. These radicals can be substituted by lower alkoxy, for example methoxy or ethoxy, or lower alkoxyethoxy, for example methoxyethoxy.

Benzyloxy radicals as detachable ether groups can be unsubstituted or substituted by one or more substituents, for example lower alkyl, such as methyl, ethyl, isopropyl or n-propyl, halogen, for example chlorine or bromine, or lower alkoxy, for example methoxy or ethoxy. These substituents are situated preferably in the ortho position or in the para-position.

Likewise detachable by solvolysis, particularly by hydrolysis or alcoholysis, in an acid medium are aliphatic ether groups substituted for their part in the α-position by an ether group, such as ethoxymethoxy, butoxymethoxy or 1-ethoxyethoxy, and particularly analogous cyclic radicals, for example 1-oxacycloalkan-2-yloxy groups, especially tetrahydrofuran-2-yloxy, also for example 4-methoxytetrahydropyran-4-yloxy.

When the solvolysis of the ether or acyl groups is performed by hydrolysis, this is carried out, depending on the nature of the detachable groups, in the presence of an organic acid, such as p-toluenesulfonic acid, or a mineral acid, such as hydrochloric acid or sulfuric acid, or in the presence of an alkali metal- or alkaline-earth metal-hydroxide or -carbonate, or in the presence of ammonia or of an amine, such as isopropylamine, or hydrazine hydrate. If solvolysis is performed by means of one of the above-mentioned acids in an alcohol, for example by means of p-toluenesulfonic acid in ethyl alcohol, solvolysis is performed by alcoholysis.

Ether groups, for example lower alkoxy groups, in particular methoxy or ethoxy, can be detached in solution or in the melt by means of a metal halide, such as aluminium halide or boron halide, for example aluminium trichloride, aluminium tribromide, boron trichloride or boron tribromide. Suitable solvents are for example benzene, nitrobenzene or ethylene chloride (cp. Jour. Chem. Soc. (1961), 1008; Ber. (1943), 76B, 900; Jour. Org. Chem. (1962), 27, 2037; Ber. (1960), 93, 2761; Jour. Am. Chem. Soc. (1968), 24, 2289; and Tetr. Lett. (1966), 4155).

Acyloxy groups detachable by acidolysis are those in which the acyl moiety is an acid radical of semi-esters of carbonic acid, for example tert-lower-alkoxycarbonyl or unsubstituted or substituted diphenylmethoxycarbonyl. Also ether groups, for example tert-lower alkoxy groups, can be detached by acidolysis. Detachment by acidolysis can be performed by treatment with suitable strong organic carboxylic acids, such as lower-alkanecarboxylic acids unsubstituted or substituted by halogen, especially by fluorine, particularly trifluoroacetic acid (if necessary in the presence of an activating agent, such as anisole), as well as with formic acid. Where no prior mention is made, the above reactions are performed in the presence of a solvent or solvent mixture, suitable reactants also being able to act as such.

An ether group detachable by reduction, especially by hydrogenolysis, is in particular an α-aryl-lower-alkyl group, such as an unsubstituted or substituted 1-phenyl-lower-alkyl group, wherein lower alkyl has up to 7 carbon atoms, and wherein substituents, especially of the phenyl moiety, can be for example lower alkyl or lower alkoxy having in each case up to 7 carbon atoms, for example methyl or methoxy, and more especially however benzyl.

The reductive detachment of the ether groups can be performed in particular for example by treatment with catalytically activated hydrogen, such as hydrogen in the presence of a suitable hydrogenating catalyst, for example a nickel, platinum or palladium catalyst, and also a rhodium or ruthenium catalyst; or the process is performed with a hydride-reducing agent, for example lithium aluminium hydride.

By acyloxy radicals detachable by hydrogenolysis are meant those groups which are detached by treatment with a chemical reducing agent (especially with a reducing metal or a reducing metal compound). Such radicals are in particular 2-halo-lower-alkoxycarbonyloxy, such as 2,2,2-trichloroethoxycarbonyloxy, which are detached for example with a reducing heavy metal, for example zinc, or with a reducing heavy metal salt, such as a chromium(II) salt, for example chromium(II) chloride or -acetate, usually in the presence of an organic carboxylic acid, such as formic acid or acetic acid.

The above reduction reactions are performed in a manner known per se, usually in the presence of an inert solvent and, if necessary, with cooling or heating, for example in a temperature range of about −20° C. to about 150° C., and/or in a closed vessel under pressure.

Depending on the ether or acyloxy group present, there is preferably selected the most mild of the described solvolysis or hydrogenolysis methods, in order to avoid changes in the pyridazinone structure.

A group protecting the amino radical, or an amino protective group, is in particular an acyl group, such as an acyl of an aliphatic, aromatic or araliphatic carboxylic acid, especially lower alkanoyl, for example acetyl or propionyl, or aroyl, for example benzoyl, or acyl of formic acid or of a carbonic acid semi-derivative, for example of a carbonic acid semi-ester, such as formyl, lower alkoxycarbonyl, for example ethoxycarbonyl or tert-butyloxycarbonyl, or aryl-lower-alkoxycarbonyl, for example benzyloxycarbonyl.

The detachment of an acyl radical used as an amino protective group can be performed in a manner known per se, for example by solvolysis, particularly by means of alcoholysis, also by means of hydrolysis. The detaching of an acyl radical by alcoholysis can be carried out for example in the presence of a strong basic agent, at elevated temperature, for example at about 50° C. to about 120° C. There is used in particular a lower alkanol, for example n-butanol or ethanol, and as a strong base an alkali metal lower alkanolate, for example a sodium or potassium lower alkanolate, for example -n-butylate or -ethylate, or an alkali metal hydroxide, for example sodium or potassium hydroxide.

Amino protective groups, for example lower-alkoxycarbonyl groups, such as tert-butyloxycarbonyl, can be detached particularly gently by acidolysis, for example by treatment with trifluoroacetic acid. A further amino protective group which can be especially mildly detached is an ethoxycarbonyl group which carries in the β-position a silyl group substituted by three hydrocarbon radicals, such as a triphenylsilyl, dimethylbutylsilyl or in particular trimethylsilyl group. A β-(trimethylsilyl)-ethoxycarbonyl group of this kind forms with the amino group to be protected a corresponding β-trimethylsilylethoxycarbonylamino group, which can be detached, under mild conditions, by reaction with fluoride ions. Reagents releasing fluoride ions are for example fluorides of quaternary organic bases, such as tetraethylammonium fluoride.

It is to be ensured that only those amino protective groups are used which can be detached selectively with retention of the desired structure of the compounds of the general formula I.

A compound of the formula I in which R is an amino group can be obtained also by selectively reducing in a compound of the formula IX

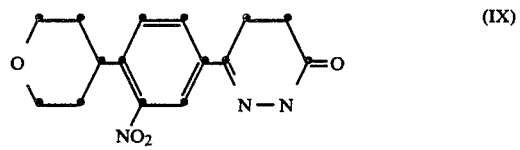

the nitro group to the amino group. Reduction is preferably performed catalytically, for example in the presence of a noble metal catalyst, such as platinum or palladium on charcoal, by means of hydrogen. Reduction can however be carried out using the methods described in the foregoing, for example with tin and hydrochloric acid, or tin(II)-chloride, the catalytic method mentioned above being however preferred.

Within the limits of the definition of the final products, substituents can be introduced, modified or detached in the compounds of the formula I obtained.

For example, resulting compounds of the formula I wherein R is a free amino group can be converted, by means of an acylating agent, for example an acetyl halide or an acetic anhydride, into compounds of the formula I wherein R is an acetylamino group. Acylation is preferably carried out in the presence of an organic base, for example in the presence of pyridine, or of a tertiary alkylamine, such as triethylamine or N-ethyl-diisopropylamine.

Furthermore, resulting compounds of the formula I in which R is a hydroxyl group can be converted, in a manner known per se, by transesterification or by etherification, into compounds of the formula I wherein R is a halogen atom or a methoxy group.

The methods described can be performed, in a customary manner, at room temperature, with cooling or heating, under normal or elevated pressure and, if necessary, in the presence or absence of a diluent, catalyst or condensation agent. The reactions can, if required, also be carried out in an inert-gas atmosphere, for example in that of nitrogen.

The starting materials are known, or, where they are new, can be produced by methods known per se. In cases in which it appeared to be of advantage, the employed starting products have already been defined after the description of the process.

Ketocarboxylic acids of the formula II can be produced using methods known per se, in the case for example of compounds of the formula II in which R is a halogen atom or a cyano group by halogenation or introduction of a cyano group in a compound of the formula X

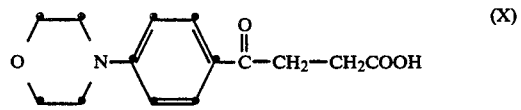

by the above-described methods, which are carried out in an analogous manner.

Compounds of the general formula III are known, or they can be obtained, using the method described by J. D. Albright et al., J. Het. Chem. 15, 881 (1978), from the corresponding ketocarboxylic acid by reaction with hydrazine. It is also possible to obtain in an analogous manner the starting compounds of the general formula IV from the corresponding aminoketocarboxylic acids. Also the starting compounds of the general formula V are known, and can be obtained for example from the corresponding dihydroxydiethyl ethers by esterification with an acid, for example a hydrohalic acid. Diethyl ether derivatives of the formula V can also be obtained from correspondingly substituted alcohols of the formula OH—CH$_2$—CH$_2$—X by etherification.

The starting compound of the formula VI and the production thereof are described for example in the German Offenlegungsschrift No. 2,207,517.

Compounds of the general formulae VIII and IX can be obtained, using the method described in the first process, from the corresponding ketocarboxylic acids by reaction with hydrazine.

The invention also relates to those embodiments of a process in which a process is discontinued at any stage, or in which a compound obtainable as an intermediate at any stage is used as the starting material and the uncompleted stages are carried out, or in which a starting material is formed under the reaction conditions or, if required, is used in the form of a salt. The invention also includes intermediates resulting therefrom.

Also embraced by the invention are therapeutic compositions consisting of an antithrombotically active proportion of a compound of the formula I together with a pharmacologically acceptable solid carrier or liquid diluent.

A resulting compound of the formula I wherein R is an amino group can, if desired, be converted into an acid addition salt in a manner known per se. There are used for producing acid addition salts in particular those acids which are suitable for the formation of therapeutically applicable salts. The following may be mentioned as examples of suitable acids: hydrohalic acids, sulfuric acids, phosphoric acids, nitric acid, perchloric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid or pyruvic acid; phenylacetic acid, benzoic acid, p-aminobenzoic acid, anthranilic acid, p-hydroxybenzoic acid, salicylic acid or p-aminosalicylic acid, embonic acid, methanesulfonic acid, ethanesulfonic acid, hydroxymethanesulfonic acid or ethylenesulfonic acid; halobenzenesulfonic acid, toluenesulfonic acid, naphthalenesulfonic acid or sulfanilic acid; and methionine, tryptophane, lysine or arginine.

Depending on the process conditions, the compound of the formula I wherein R is an amino group can occur also as an acid addition salt.

The acid addition salts of the novel compounds can be converted, in a manner known per se, into the free compound, for example with basic agents, such as alkalies or ion exchangers. On the other hand, the free bases obtained can form salts with organic or inorganic acids.

The pharmaceutical preparations according to the invention contain at least one compound of the formula I as active ingredient, together with a customary pharmaceutical carrier. The nature of the carriers used is governed largely by the field of application. The pharmaceutical compositions according to the invention, which contain compounds of the formula I as active ingredients, can be administered orally, parenterally or rectally.

Suitable for oral treatment of thrombosis are in particular solid dosage units, such as tablets, dragees and capsules, which preferably contain between 10 and 90% of an active substance of the general formula I in order to render possible the administration of daily doses of between 1.0 and 1000 mg/kg, preferably between 2 and 100 mg/kg, particularly between 5 and 10 mg/kg, to warm-blooded animals having a body weight of about 70 kg. Tablets and dragee cores are produced by combining the compounds of the formula I with solid pulverulent carriers, such as lactose, saccharose, sorbitol, maize starch, potato starch or amylopectin, cellulose derivatives or gelatine, preferably with the addition of lubricants, such as magnesium or calcium stearate, or polyethylene glycols of suitable molecular weight. Dragee cores are subsequently coated for example with concentrated sugar solutions which can also contain for example gum arabic, talcum and/or titanium dioxide, or with a lacquer dissolved in readily volatile organic solvents or solvent mixtures. Colouring agents may be added to these coatings, for example for identification of the various dosage amounts. Soft gelatine capsules and other closed capsules consist for example of a mixture of gelatine and glycerin, and can contain for example mixtures of a compound of the formula I with polyethylene glycol. Hard gelatine capsules contain for example granulates of an active substance with solid pulverulent carriers, such as lactose, saccharose, sorbitol or mannitol; starches, such as potato starch, maize starch or amylopectin, cellulose derivatives as well as magnesium stearate or stearic acid.

Suitable dosage units for rectal administration are for example suppositories which consist of a combination of an active substance with a suppository foundation substance based on natural or synthetic triglycerides (for example cocoa butter), polyethylene glycols or suitable higher fatty alcohols; and gelatine rectal capsules which contain a combination of the active substance with polyethylene glycols.

For liquids to be taken orally, such as syrups and elixiers, the concentration of active substance is chosen to ensure that a single dose can be easily measured out, for example as the content of a tea-spoon or of a measuring spoon, for example 5 ml, or as a multiple of these amounts.

The following Examples (a) to (e) are intended to illustrate some typical forms of application, but in no way do they represent the only embodiment thereof.

(a) 100.0.g of active substance are mixed with 610.0 g of lactose and 422.0 g of potato starch; the mixture is then moistened with an alcoholic solution of 8 g of gelatine, and is granulated through a sieve. The granulate is dried, and 60.0 g of talcum, 10.0 g of magnesium stearate and 20.0 g of colloidal silicon dioxide are mixed in; and the mixture is subsequently pressed to form 10,000 tablets, each weighing 125 mg and each containing 10 mg of active substance. The tablets can, if desired, be provided with grooves for a more precise adjustment of the dosage amount.

(b) A granulate is prepared from 100.0 g of active substance, 379 g of lactose and the alcoholic solution of 6.0 g of gelatine; after drying, the granulate is mixed with 10.0 g of colloidal silicon dioxide, 40.0 g of talcum, 60.0 g of potato starch and 5.0 g of magnesium stearate, and the mixture is pressed out to form 10,000 dragee cores. These are subsequently coated with a concentrated syrup prepared from 533.5 g of crystallised saccharose, 20.0 g of shellac, 75.0 g of gum arabic, 250.0 g of talcum, 20.0 g of colloidal silicon dioxide and 1.5 g of colouring agent, and finally dried. The dragees obtained each weigh 150 mg and each contain 10 mg of active substance.

(c) 10.0 g of active substance and 1990 g of finely ground suppository foundation substance (for example cocoa butter) are thoroughly mixed and then melted. The melt is maintained homogeneous by stirring whilst 1000 2.0 g suppositories each containing 25 mg of active substance are being poured.

(d) To prepare a syrup having a content of active substance of 0.25%, there are dissolved in 3 liters of distilled water 1.5 liters of glycerin, 42 g of p-hydroxybenzoic acid methyl ester, 18 g of p-hydroxybenzoic acid-n-propyl ester and, with slight warming, 25.0 g of active substance; to this solution are then added 4 liters of 70% sorbitol solution, 1000 g of crystallised saccharose, 350 g of glucose and an aroma substance, for example 250 g of "Orange Peel Soluble Fluid", Eli Lilly and Co., Indianapolis, or 5 g of natural lemon aroma and 5 g of "half and half" essence, both from Haarmann and Reimer, Holzminden, Germany; the solution obtained is filtered, and the filtrate is subsequently made up with distilled water to 10 liters.

(e) To prepare a drip solution containing 1.5% of active substance, 150.0 g of active substance and 30 g of sodium cyclamate are dissolved in a mixture of 4 liters of ethanol (96%) and 1 liter of propylene glycol. A mixture of 3.5 liters of 70% sorbitol solution and 1 liter of water is prepared separately and is then added to the above solution of active substance. An aroma substance, for example 5 g, of cough-sweet aroma or 30 g of grapefruit essence, both from Haarmann and Reimer, Holzminden, Germany, is added; the whole is well mixed, filtered, and made up with distilled water to 10 liters.

The Examples which follow further illustrate the production of the novel compounds of the formula I, but in no way do they limit the scope of the invention. The temperature values are in degrees Centigrade.

EXAMPLE 1

The solution of 0.3 ml of bromine in 4.5 ml of chloroform is added at 0° C., with stirring, to a solution of 1.5 g of 6-(4-morpholino-phenyl)-4,5-dihydro-3(2H)-pyridazinone in 11 ml of chloroform. The reaction solution is further stirred for 30 minutes at 0° C. and for 60 minutes at room temperature; and is then shaken, in a separating funnel, with 1N sodium bicarbonate solution until two clear phases are formed. The organic phase is washed with water, dried over sodium sulfate and concentrated by evaporation. The yield is 1.9 g of crude 6-(4-morpholino-3-bromophenyl)-4,5-dihydro-3(2H)-pyridazinone. For further purification, this is dissolved, with the addition of a small amount of methylene chloride, in 100 ml of ethyl acetate. The solution is washed three times with 2N hydrochloric acid, and is then extracted with 5N hydrochloric acid. There are then obtained from these extracts, after adjustment with sodium hydroxide solution to give a basic reaction, extraction with ethyl acetate/methylene chloride, washing, drying and concentration of the organic phases by evaporation, 1.3 g of purified product which, after recrystallisation from ethanol, melts at 175°–176° C.

EXAMPLE 2

90 g of 6-(4-morpholino-3-nitrophenyl)-4,5-dihydro-3(2H)-pyridazinone (J.Het.Chem. 15, 881 (1978)) are hydrogenated in 2.7 liters of ethanol with 9 g of a 5% palladium on charcoal catalyst at room temperature under normal pressure. The reaction mixture is filtered, and the ethanol filtrate is concentrated by evaporation. The catalyst is suspended in 1N hydrochoric acid, filtered off, and then washed with 1N hydrochloric acid. The pH-value of the aqueous phases is adjusted to 6 with concentrated sodium hydroxide solution, and the product which has precipitated is filtered off with suction and washed with water. The product thus obtained is combined with the evaporation residue of the ethanol filtrate, and the whole is dissolved in dimethylformamide with heating; the solution is treated with active charcoal and filtered through Hyflo; there is then crystallised out from the filtrate, by cooling and the addition of water, 6-(3-amino-4-morpholino-phenyl)-4,5-dihydro-3(2H)-pyridazinone, which, after drying at 100° C. under high vacuum, melts at 249°–253° C.

EXAMPLE 3

7 g of 3-fluoro-4-morpholino-benzoylpropionic acid together with 1.32 ml of hydrazine hydrate and 90 ml of ethanol are refluxed for 2 hours. The reaction mixture is cooled to 0° C.; it is further stirred for one hour at this temperature, and the crystals which have precipitated are filtered off with suction and subsequently washed with small amounts of ethanol. The crystals are dried at 50° C. under high vacuum to thus obtain 6.25 g of 6-(3-fluorophenyl-4-morpholino)-4,5-dihydro-3(2H)-pyridazinone having a melting point of 167°–170° C.

The 3-fluoro-4-morpholino-benzoylpropionic acid used as starting material is produced as follows:

33 g of 3,4-difluoro-benzoylpropionic acid (obtained by Friedel-Crafts acylation of 1,2-difluorobenzene with succinic anhydride in the presence of aluminium chloride) together with 60 ml of morpholine are heated at 150° C. for 20 hours with stirring. The reaction mixture is cooled, dissolved in ethylacetate, and this solution is washed with 2N hydrochloric acid and extracted with 5N hydrochloric acid. The pH-value of the 5N hydrochloric acid extracts is brought to 6 with concentrated sodium hydroxide solution, and the suspension formed is extracted with ethyl acetate. The organic phases are washed with water, dried over sodium sulfate and concentrated by evaporation. The crystalline residue (31.7 g) together with 18 g of potassium hydroxide, 180 ml of water and 180 ml of ethanol is refluxed for 10 hours; it is then cooled, concentrated by evaporation and distributed between water and ethyl acetate. The pH-value of the aqueous phases is adjusted to 5, and the 3-fluoro-4-morpholino-benzoylpropionic acid which has precipitated is filtered off under suction and dried (m.p. 164°–168° C.).

EXAMPLE 4

5.8 g of 4-morpholino-3-trifluoromethylbenzoylpropionic acid-morpholineamide together with 2.2 ml of hydrazine hydrate and 90 ml of 50% acetic acid are refluxed for 1 hour. The reaction mixture is cooled, concentrated in a rotary evaporator, and a small amount of water is added; the pH-value is adjusted to 6 with a 2N sodium carbonate solution, and the mixture is extracted with methylene chloride. The methylene chloride extracts are washed with water, dried over sodium sulfate and concentrated by evaporation. From the residue is obtained, by recrystallisation from ethanol/petroleum ether, 6-(3-trifluoromethyl-4-morpholinophenyl)-4,5-dihydro-3(2H)-pyridazinone, m.p. 163°–166° C.

The 4-morpholino-3-trifluoromethyl-benzoylpropionic acid-morpholineamide required as starting material is produced as follows:

12.3 g of o-(4-chloro-3-trifluoromethyl-phenyl)-4-morpholino-acetonitrile (J. Het. Chem. 15, 883 (1978)) are dissolved in 150 ml of tetrahydrofuran, and at 5° C. are added, with stirring, 5 ml of 30% ethanolic potassium hydroxide solution. The reaction mixture is stirred for a further 15 minutes at 5° C., and there is then added dropwise, under the same conditions, the solution of 5.9 g of ethyl acrylate in 100 ml of tetrahydrofuran. The reaction mixture is further stirred for 1 hour at room temperature, and subsequently concentrated in a rotary evaporator. To the residue obtained is added toluene three times, and this is again evaporated off in the rotary evaporator. The residue thus obtained is taken up in ether and filtered until clear. The filtrate is concentrated by evaporation to yield 14.3 g of crude γ-cyano-γ-(4chloro-3-trifluoromethyl-phenyl)-γ-(4-morpholino)-ethyl butyrate, which is saponified in two stages as follows:

12.3 g of γ-cyano-γ-(4-chloro-3-trifluoromethyl-phenyl)-γ-(4-morpholino)-ethyl butyrate together with 75 ml of acetic acid and 32 ml of water are heated for 2 hours at 100° C. The reaction mixture is concentrated in a rotary evaporator, and the residue is dissolved in 250 ml of ethanol and 9.2 ml of water. The reaction mixture is rendered alkaline with solid potassium hydroxide; a further 1.9 g of solid potassium hydroxide are added, and stirring is maintained for 30 minutes whilst the reaction mixture is being refluxed, and subsequently for 16 hours at room temperature.

The reaction mixture is concentrated by evaporation, and the residue is distributed between ethyl acetate and water; the aqueous phases are then rendered acidic with concentrated hydrochloric acid, and extracted with ethyl acetate. From this extract are obtained, after concentration by evaporation, 6.2 g of 4-chloro-3-trifluoromethyl-benzoylpropionic acid having a melting point of 87°–96° C. The unpurified material is directly used further as follows:

3 g of 4-chloro-3-trifluoromethyl-benzoylpropionic acid together with 6.5 ml of morpholine are refluxed for 20 hours. The reaction mixture is cooled, taken up in ethyl acetate, washed with 1N hydrochloric acid and water, dried over sodium sulfate and concentrated by evaporation. There are obtained as residue 3.2 g of unpurified 4-morpholino-3-trifluoromethyl-benzoylpropionic acidmorpholineamide, which can be further used directly. Crystals having a melting point of 76°–79° C. are obtained after recrystallisation from a mixture of ether and petroleum ether.

EXAMPLE 5

The solution of 3.5 ml of acetic anhydride in 30 ml of dimethylformamide is added dropwise to a suspension of 10 g of 6-(3-amino-4-morpholino-phenyl)-4,5-dihydro-3(2H)-pyridazinone (obtained according to Example 6), 6.2 ml of diisopropylethylamine and 120 ml of dimethylformamide. The reaction mixture is further stirred for 48 hours at room temperature, and then concentrated in a rotary evaporator. The residue is distributed between ethyl acetate and 2N hydrochloric acid. The hydrochloric acid extracts are combined, and rendered basic with concentrated sodium hydroxide solution. The product which precipitates is filtered off with suction, washed with water and dried under high vacuum. The yield after recrystallisation from dimethylformamide/ethanol and purification through active charcoal is 7.5 g of 6-(3-acetamino-4-morpholino-phenyl)-4,5-dihydro-3(2H)-pyridazinone having a melting point of 240°–242° C.

EXAMPLE 6

2.2 g of 6-(4-amino-3-methyl-phenyl)-4,5-dihydro-3(2H)-pyridazinone together with 5.5 ml of diisopropylethylamine, 3.7 g of dibromodiethyl ether and 11 ml of dimethylformamide are stirred at 100° C. for 6 hours. The reaction mixture is cooled to room temperature, and ethyl acetate is added. The diisopropylamine hydrobromide which has precipitated is filtered off with suction, and washed with ethyl acetate. The combined filtrates are washed with water, dried over sodium sulfate and concentrated by evaporation. The residue is chromatographed through silica gel. After separation of non-polar impurities with a mixture of toluene:ethyl acetate=1:1, the 6-(4-morpholino-3-methyl-phenyl)-4,5-dihydro-3(2H)-pyridazinone is eluted with ethyl acetate, and melts at 208°–211° C. after recrystallisation from a mixture of methylene chloride/petroleum ether.

The 6-(4-amino-3-methyl-phenyl)-4,5-dihydro-3(2H)-pyridazinone required as starting material is produced as follows:

There are obtained from 70 g of N-acetyl-1,2-toluidine, with 47 g of succinic anhydride and 234 g of aluminum chloride in 2000 ml of tetrachlorethane, by the customary method, 50 g of 3-(3-methyl-4-acetamido-benzoyl)-propionic acid, m.p. 150°–160° C., as crude product. From this are obtained, by hydrolysis in 18% hydrochloric acid, 28 g of crude 3-(4-amino-3-methyl-benzoyl)-propionic acid. And from 6 g of 3-(4-amino-3-methyl-benzoyl)-propionic acid are obtained, with 1.7 ml of hydrazine hydrate in 70 ml of ethanol, in a manner analogous to that in Example 1, 2.6 g of 6-(4-amino-3-methyl-phenyl)-4,5-dihydro-3(2H)-pyridazinone having a melting point of 215°–225° C.

EXAMPLE 7

25 g of 3-amino-4-morpholino-benzoylpropionic acid are dissolved in 24.2 g of concentrated hydrochloric acid and 70 ml of water, and the solution is diazotised at 0° C. with a solution of 7.7 g of sodium nitrile in 40 ml of water. A reagent (produced by mixing a solution of 27 g of potassium cyanide in 50 ml of water with the solution, heated to 60° C., of 24.2 g of copper sulfate pentahydrate in 95 ml of water) is cooled to room temperature, and is added to the diazonium solution at 0°–5° C. The reaction mixture is afterwards stirred for 16 hours at room temperature; it is then diluted with water, adjusted to pH 14 with concentrated sodium hydroxide solution, and washed three times with ethyl acetate. The aqueous phases are purified with active charcoal, adjusted to pH 2 with concentrated hydrochloric acid, and extracted with ethyl acetate. The organic extracts are filtered clear, washed with 2N hydrochloric acid and with water, dried over sodium sulfate and concentrated by evaporation. The yield is 16 g of crude 3-cyano-4-morpholino-benzoylpropionic acid, which is reacted with hydrazine hydrate in a manner analogous to that in Example 1. There is thus obtained 6-(3-cyano- 4-morpholino-phenyl)-4,5-dihydro-3(2H)-pyridazinone, m.p. 212°-214° C., recrystallised from methylene chloride/dimethylformamide.

The 3-amino-4-morpholino-benzoylpropionic acid required as starting material is obtained by reaction of 3-nitro-4-chlorobenzoylpropionic acid with morpholine, analogously to Example 8, and reduction of the formed 3-nitro-4-morpholino-benzoylpropionic acid.

What is claimed is:

1. A pyridazinone of the general formula I

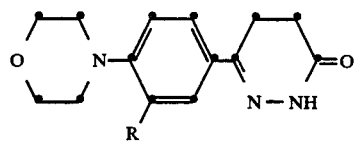

wherein R is a bromine atom, or the cyano, group, and the tautomeric forms thereof.

2. A compound of the general formula I of claim 1 being 6-(3-cyano-4-morpholino-phenyl)-4,5-dihydro-3(2H)-pyridazinone, and the tautomeric forms thereof.

3. The compound of claim 1 wherein R is bromine.

4. A therapeutic composition for the treatment of thrombotic diseases comprising an effective amount of an antithrombotic active compound of formula I as claimed in claim 1 together with a pharmaceutically acceptable excipient.

5. A therapeutic composition as defined in claim 4, wherein in the antithrombotic active compound is 6-(3-cyano-4-morpholino-phenyl)-4,5-dihydro-3(2H)-pyridazinone or a tautomeric form thereof.

* * * * *